(12) United States Patent
Nishio et al.

(10) Patent No.: US 7,572,010 B2
(45) Date of Patent: Aug. 11, 2009

(54) CORNEA IMAGING APPARATUS

(75) Inventors: Masato Nishio, Nagoya (JP); Yusaku Ito, Ama-gun (JP)

(73) Assignee: Tomey Corporation, Nagoya (JP)

( * ) Notice: Subject to any disclaimer, the term of this patent is extended or adjusted under 35 U.S.C. 154(b) by 31 days.

(21) Appl. No.: 11/882,387

(22) Filed: Aug. 1, 2007

(65) Prior Publication Data
US 2008/0055544 A1 Mar. 6, 2008

(30) Foreign Application Priority Data
Aug. 31, 2006 (JP) .............................. 2006-236209

(51) Int. Cl.
*A61B 3/14* (2006.01)
*A61B 3/10* (2006.01)

(52) U.S. Cl. ..................... 351/208; 351/205; 351/206

(58) Field of Classification Search .......... 351/200–221
See application file for complete search history.

(56) References Cited

U.S. PATENT DOCUMENTS 5,436,679 A * 7/1995 Ohtsuka et al. ............. 351/206
2007/0263172 A1* 11/2007 Mura ......................... 351/208

FOREIGN PATENT DOCUMENTS

| JP | A 07-079924 | 3/1995 |
| JP | B2 2831538 | 9/1998 |
| JP | A-11-206715 | 8/1999 |
| JP | A-2002-017679 | 1/2002 |
| JP | A-2003-153860 | 5/2003 |
| WO | WO 03/015623 A2 | 2/2003 |
| WO | WO 2006/006048 A1 | 1/2006 |

* cited by examiner

*Primary Examiner*—Mohammed Hasan
(74) *Attorney, Agent, or Firm*—Oliff & Berridge, PLC

(57) ABSTRACT

A cornea imaging apparatus comprising: an illumination optical system having an illumination source; an imaging optical system having a photoelectric element for receiving a reflected light beam from a cornea of an eye under examination; actuating means for moving the illumination optical system and the imaging optical system in a direction nearer to or further from the eye to bring about focusing; imaging process retracting control means for controlling the actuating means during an imaging operation by the imaging optical system; continuous imaging means for taking multiple images of the cornea at different times and positions by the photoelectric element of the imaging optical system during a retracting operation; and imaging operation control means for controlling imaging operation status of the cornea by the continuous imaging means with reference to a photoreception signal of reflected light from the cornea.

22 Claims, 11 Drawing Sheets

CORNEA IMAGING APPARATUS

INCORPORATED BY REFERENCE

The disclosure of Japanese Patent Application No. 2006-236209 filed on Aug. 31, 2006 including the specification, drawings and abstract is incorporated herein by reference in its entirety.

BACKGROUND OF THE INVENTION

1. Field of the Invention

The present invention relates to a cornea imaging apparatus for imaging an cornea of the eye by means of directing illumination into an eye being examined and receiving the light reflected from the cornea of the eye being examined.

2. Description of the Related Art

To date, observation of the cornea of the eye, and in particular of the cellular status of the corneal endothelium, has been commonly carried out when determining the presence of ocular disorders, in the course of eye surgery, and similar situations.

A cornea imaging apparatus capable, through a noncontact method, of imaging the cells of the corneal endothelium of the eye under examination during such observation of the cellular status of the corneal endothelium are known in the art. This cornea imaging apparatus is designed to direct a slit beam of illumination light from an optical system onto the cornea of the eye under examination, and receive the light reflected from the cornea in order to image the cells of the corneal endothelium.

However, a problem with such cornea imaging apparatus has been that, owing to the small thickness dimension of the corneal endothelial cells, it is frequently difficult to obtain a sharp focused image of the corneal endothelial cells. Particularly since such cornea imaging apparatus employ a slit beam of illumination light, it is necessary to accurately align the illumination optical system and the imaging optical system at the focal position of the endothelium in the near/far direction with respect to the corneal endothelial cells, in order to avoid the adverse effects of light reflected by the epithelium and parenchyma of the cornea.

Accordingly, there has proposed in the past, for example, in Patent Document 1 (U.S. Pat. No. 5,436,679), an apparatus employing a line sensor for detecting the distribution of intensity of reflected light from the cornea, detecting the focal position of the corneal endothelial cells, and aligning the optical system with it. Specifically, by taking into consideration the distribution characteristics of the intensity of reflected light in the cornea, which is composed of the corneal epithelium, parenchyma, and endothelium, the focal position of the corneal endothelial cells is estimated from the location of the peak in the output values of the line sensor. The corneal endothelial cells are then imaged with the illumination optical system and the imaging optical system aligned with this estimated focal position.

However, a problem with the cornea imaging apparatus of the prior art design like that disclosed in Patent Document 1 is the difficulty of detecting with consistent accuracy the focal position of the corneal endothelial cells. Specifically, since differences in corneal thickness exist among individuals, including for example instances of reduced corneal thickness as a result of corrective surgery for refractive errors or the like, where the cornea is thin it is difficult in practice to detect both the peak of the epithelium and of the endothelium, with the risk of an inability to correctly identify the endothelial focal position. There also exists a risk that, due to the properties of the corneal parenchyma, and in particular to clouding of the parenchyma caused by ocular disease or the like, conflicting levels of reflection by the parenchyma and the endothelium may make it impossible to detect focal position from the peak of the endothelium, or result in erroneous location detection.

Furthermore, even if focal position is successfully detected with good accuracy, since the imaging process is carried out subsequent to alignment with the estimated focal position detected by the line sensor, slight movements of the eye may throw off the focal position, with the risk that a sharp focused image of the endothelium will not be obtained.

In Patent Document 2 (Japanese Pat. No. 2831538) for example, there is disclosed a cornea imaging apparatus constituted so as to move the optical system forward in the direction nearer to the eye under examination; to first detect the focal position with respect to the epithelium; and from the focal position with respect to the epithelium; to then estimate the focal position of the corneal endothelial cells based on anatomical thickness of the cornea. In this cornea imaging apparatus, first, the optical system is moved in the direction nearer to the eye under examination while directing illumination into the eye under examination. Then, after detecting the focal position with respect to the epithelium by means of detected reflected light from the epithelium, the focal position is moved towards the endothelium by a distance depending on the distance separating the endothelium from the epithelium, which distance was established previously on the basis of anatomical thickness of the cornea. The focal position is thereby aligned with the corneal endothelial cells.

However, accurate detection of the focal position of the corneal endothelial cells proved difficult to detect with the cornea imaging apparatus disclosed in Patent Document 2 as well. Specifically, as noted above, there are differences in corneal thickness among individuals, and since the distance between the epithelium and the endothelium will differ according to the patient under examination as well, the correct position will not necessarily be attained simply by moving the optical system from the epithelium towards the endothelium by a preset distance. Moreover, while the cornea imaging apparatus in question is adapted to perform continuous imaging over a wide range in consideration of such individual differences, reliable imaging of the corneal endothelial cells requires carrying out continuous imaging over a wide range able to encompass individual differences, and the imaging will be time-consuming. A resultant problem is that the subject under examination must keep his or her eyes open while being exposed to bright illumination, and thus prolonged imaging time will impose considerable strain on the patient.

SUMMARY OF THE INVENTION

It is therefore an object of the present invention to provide a cornea imaging apparatus of novel construction affording faster and more accurate detection of the focal position of the corneal endothelial cells, while permitting imaging to be performed with higher accuracy.

The above and/or optional objects of this invention may be attained according to at least one of the following modes of the invention. The following modes and/or elements employed in each mode of the invention may be adopted at any possible optional combinations. It is to be understood that the principle of the invention is not limited to these modes of the invention and combinations of the technical features, but may otherwise be recognized based on the teachings of the present invention disclosed in the entire specification and drawings or that may be recognized by those skilled in the art in the light of the present disclosure in its entirety.

A first mode of the invention provides a cornea imaging apparatus comprising: an illumination optical system having an illumination source for directing a slit light beam on a diagonal into an eye under examination; an imaging optical system having a photoelectric element for receiving a reflected light beam produced by reflection of the slit light beam from a cornea of the eye under examination, and for imaging the cornea; actuating means for moving the illumination optical system and the imaging optical system in totality in a direction nearer to or further from the eye under examination to bring about focusing; imaging process retracting control means for controlling the actuating means during an imaging operation by the imaging optical system, to retract the illumination optical system and the imaging optical system in a direction away from the eye under examination in a cross direction of the eye under examination; continuous imaging means for taking multiple images of the cornea at different times and positions by the photoelectric element of the imaging optical system during a retracting operation by the imaging process retracting control means; and imaging operation control means for controlling imaging operation status of the cornea by the continuous imaging means during the retracting operation by the imaging process retracting control means, with reference to a photoreception signal of reflected light from the cornea of the eye under examination.

In the cornea imaging apparatus constructed in accordance with this mode, the illumination optical system and the imaging optical system are retracted in the direction away from the eye under examination by means of the imaging process retracting control means, and therefore the apparatus is not affected by reflected light from the corneal parenchyma etc. Specifically, since the region behind the cornea is filled with the aqueous humor, behind the cornea there will be substantially no reflection of the light beam from the illumination source, and commensurate reflected light will be obtained only once the back edge of the cornea is reached. It will be possible thereby to clearly detect reflected light from the cornea, and with reference to this reflected light to stabilize operation of the imaging operation control means which controls the imaging operation status. Moreover, since the imaging operation is controlled on the basis of reflected light from the eye under examination, it will be possible to respond flexibly to individual differences in corneal thickness among patients being examined, and to carry out operational control in an efficient manner.

Additionally, by means of continuous imaging of the cornea, it will be possible to acquire multiple images of the cornea over a prescribed range. It is possible thereby to effectively prevent imaging errors, through synergistic action with the stabilization of the imaging operation mentioned previously.

It is possible to employ any of various control modes as the mode for controlling the imaging operation status by the imaging operation control means. For example, by initiating continuous imaging in response to the photoreception signal of reflected light from the corneal endothelial cells located at the back edge of the cornea, it will be possible to image the corneal endothelial cells with a high degree of accuracy and excellent efficiency. Furthermore, the mode of control of the imaging operation status is not limited to control of initiation of continuous imaging in this way, and may instead involve changing the time interval of continuous imaging, the intensity of the illumination source, the speed of the optical system retracting operation, etc., with reference to a photoreception signal of reflected light from the cornea.

A second mode of the invention provides the cornea imaging apparatus according to the first mode, wherein the illumination sources of the illumination optical system comprises an imaging light source for imaging the cornea by means of guiding, into the photoelectric element of the imaging optical system, reflected light that has been directed into the eye under examination and reflected from the cornea; and with an output signal by the photoelectric element of reflected light produced by reflection by the cornea of an illuminating light beam from the imaging light source utilized as the photoreception signal, a cornea imaging operation status is controlled in the imaging operation control means on the basis of the output signal of the photoelectric element.

In the cornea imaging apparatus constructed in accordance with this mode, reflected light from the cornea can be received using the photoelectric element that also performs imaging of the cornea. A simpler design is possible thereby.

A third mode of the invention provides the cornea imaging apparatus according to the second mode, wherein with the output signal by the photoelectric element utilized as the photoreception signal, the cornea imaging operation status is controlled in the imaging operation control means on the basis of the output signal of the photoelectric element by means of controlled modification of a speed of the retracting operation by the imaging process retracting control means.

In the cornea imaging apparatus constructed in accordance with this mode, the number of images taken in continuous imaging can be adjusted by means of modifying the speed of the retracting operation. Moreover, it is possible to carry out operation control in a more efficient manner. For example, the optical system could be retracted at relatively high speed from the rear of the cornea, and then switched to relatively slow speed at the point in time that reflected light from the cornea is first received, thereby affording quick alignment of the optical system with the cornea, as well as shorter imaging time.

A fourth mode of the invention provides the cornea imaging apparatus according to the second or third mode, wherein with the output signal by the photoelectric element utilized as the photoreception signal, the cornea imaging operation status is controlled in the imaging operation control means on the basis of the output signal of the photoelectric element by means of controlled modification of a continuous imaging time interval of the cornea by the continuous imaging means.

In the cornea imaging apparatus constructed in accordance with this mode, the number of images taken in continuous imaging can be adjusted by means of modifying the time interval in continuous imaging. For example, imaging could be carried out at relatively long time intervals up to the point that reflected light from the cornea is received, and imaging then carried out at relatively short time intervals from the point in time that reflected light from the cornea is first received.

A fifth mode of the invention provides the cornea imaging apparatus according to any of the first to fourth modes, wherein a position-sensing light source is employed as one of the illumination sources of the illumination optical system, separate from the imaging light source used for imaging the cornea by means of guiding, into the photoelectric element of the imaging optical system, reflected light that has been directed into the eye under examination and reflected from the cornea; a line sensor for receiving the reflected light produced by reflection by the cornea of the illuminating light beam is employed as the position-sensing light source; and with the output signal by the line sensor as utilized as the photoreception signal, the cornea imaging operation status is controlled in the imaging operation control means on the basis of the output signal of the line sensor.

In the cornea imaging apparatus constructed in accordance with this mode, through the use of the line sensor it is possible to detect the intensity distribution of reflected light from each layer of the cornea, i.e. the epithelium, the parenchyma, the endothelium and so on. It is possible thereby to carry out more accurate operational control, on the basis of the intensity distribution of the corneal layers. In the present mode, a light source of lower illumination intensity than the imaging light source is will preferably be employed as the position-sensing light source. This arrangement makes it possible to reduce the burden on the patient by using this low-intensity position-sensing light source at times other than imaging of the cornea, such as during alignment of the optical system for example. More preferably, a light source that emits an infrared beam will be employed as the position-sensing light source. With this arrangement, it is possible to further reduce the burden on the patient, since the patient will not perceive the illuminating beam produced by the position-sensing light source. As in the first mode described previously, any of various control modes could be employed as the mode for controlling the imaging operation status by the imaging operation control means.

A sixth mode of the invention provides the cornea imaging apparatus according to the fifth mode, wherein in the imaging operation control means, emission of light by the imaging light source and a cornea imaging operation by the continuous imaging means are controlled so as to be respectively initiated on a condition that reflected light from the cornea has been verified on the basis of the output signal of the line sensor.

In the cornea imaging apparatus constructed in accordance with this mode, improved operational control which takes into consideration the relative positions of the optical system and the cornea can be carried out on the basis of reflected light from the cornea detected by the line sensor. It is possible thereby the avoid prolonged emission of light by the imaging light source, the reducing the burden on the patient, as well as affording more reliable imaging.

A seventh mode of the invention provides the cornea imaging apparatus according to the sixth mode, wherein in the imaging operation control means, a detection level of an output signal is set to one corresponding to a prescribed intensity lower than that of an output signal corresponding to reflected light intensity at a focal location from a corneal endothelium detected by the line sensor. Further, emission of light by the imaging light source in the imaging operation control means and the cornea imaging operation by the continuous imaging means are controlled so as to be respectively initiated on the condition that the output signal of the line sensor receiving the reflected light of the cornea has reached this detection level.

In the cornea imaging apparatus constructed in accordance with this mode, by initiating continuous imaging at a point in time that an output signal lower than the reflected light intensity at the focal location is received, continuous imaging can be initiated from a position somewhat rearward of the focal position of the corneal endothelium. The corneal endothelium can be imaged more reliably thereby.

An eighth mode of the invention provides the cornea imaging apparatus according to any of the first to seventh modes, further comprising: pre-imaging process advancing control means for controlling the actuating means and advancing the illumination optical system and the imaging optical system in a direction closer to the eye under examination in the cross direction of the eye under examination, prior to the retracting operation by the imaging process retracting control means during the imaging operation; and reversal operation control means for controlling reversal of a direction of movement from advancing operation by the pre-imaging process advancing control means to the retracting operation by the imaging process retracting control means, on the basis of the photoreception signal of reflected light from the cornea of the eye under examination.

In the cornea imaging apparatus constructed in accordance with this mode, an operation reversing the optical systems that have been advanced by the pre-imaging process advancing control means is performed on the basis of reflected light actually reflected from the cornea of the eye under examination, whereby the reversal operations can be carried out at accurate positions reflective of individual differences among eyes under examination. Efficient imaging operations can thus be carried out more accurately for individual eyes under examination.

It would be possible to employ appropriately any of various modes as the specific mode for controlling the reversal operation on the basis of reflected light from the cornea. For example, it would be possible to employ appropriately reflected light from each of the layers making up the cornea, such as the epithelium or the endothelium, as the reflected light from the cornea. The photoelectric element mentioned earlier could be used as the means for receiving this reflected light; it would also be acceptable to use the line sensor taught in the fifth mode. In preferred practice, there will be employed a mode wherein the illumination optical system and the imaging optical system are advanced further by a prescribed distance, such as the anatomical thickness of the cornea, from the location at which reflected light from the epithelium is detected, thereby positioning the optical system focal position to the rear of cornea; and the retracting operation is initiated with this position as the reversal position.

A ninth mode of the invention provides the cornea imaging apparatus according to the eighth mode, wherein a position-sensing light source is employed as one of the illumination sources of the illumination optical system, separate from the imaging light source used for imaging the cornea by means of guiding, into the photoelectric element of the imaging optical system, reflected light that has been directed into the eye under examination and reflected from the cornea; the line sensor for receiving the reflected light produced by reflection by the cornea of the illuminating light beam is employed as the position-sensing light source; an output signal of the line sensor is used as the photoreception signal of reflected light from the cornea of the eye under examination; and on the basis of the output signal of the line sensor, the direction of movement during the advancing operation by the pre-imaging process advancing control means is reversed by the reversal operation control means, at a reversal position established to a rear of an endothelium focal position.

In the cornea imaging apparatus constructed in accordance with this mode, the distribution of reflected light intensity from the corneal layers can be detected using the line sensor, and operation control can then be carried out on the basis of the intensity distribution. Consequently, when detecting a prescribed layer such as the epithelium for example, if an arrangement using only the photoelectric element of the preceding eighth mode were employed, it would only be possible to detect reflected light from the specific layer at a specific point in time. Whereas by using a line sensor in place of the photoelectric element or together with the photoelectric element, it will be possible to detect the intensity distribution of reflected light from each layer throughout a prescribed thickness dimension. Consequently, a layer of interest can be detected more accurately based on a comparison with reflected light intensity from the other layers, and thus the reversal position can be established with greater accuracy. It is possible thereby to set the reversal position to a position to rear of the endothelium focal position, and to more accurately image the corneal endothelial cells. An example of a specific mode for reversal control based on the output signal from the line sensor would be, for example, to set the reversal position at a position advanced past the position of the epithelium by a prescribed distance, such as the equivalent of the anatomical thickness of the cornea.

A tenth mode of the invention provides the cornea imaging apparatus according to any of the first to ninth modes wherein in the imaging operation control means, the imaging operation is terminated by the continuous imaging means on the basis of at least one condition selected from a distance of movement of the illumination optical system and the imaging optical system, the photoreception signal of reflected light from the cornea of the eye under examination, and elapsed time.

In the cornea imaging apparatus constructed in accordance with this mode, by means of terminating continuous imaging on the basis of the aforementioned conditions, the time required for continuous imaging can be reduced, the efficiency of imaging can be improved, and the burden on the patient can be reduced.

While it is possible for the specific content of the aforementioned conditions to be established appropriately, for example, with regard to the distance of movement of the optical systems, imaging can be terminated at the point in time when the optical systems have moved from the location where the retracting operation was initiated, by a distance somewhat greater than anatomical cornea thickness; or with regard to elapsed time, continuous imaging can be terminated once a prescribed time interval has elapsed since initiating the retracting operation. With regard to the photoreception signal of reflected light, imaging could be terminated at the point in time when reflected light is no longer actually received; or the position of the epithelium could be detected from reflected light of the cornea by the line sensor defined in the fifth mode, and imaging could be terminated at the point in time that the optical systems reach the position of the epithelium.

An eleventh mode of the invention provides the cornea imaging apparatus according to any of the first to tenth modes, further comprising: memory means for saving photographic images taken by the photoelectric element; and image selecting means for sorting photographic images on the basis of photographic image light intensity level, contrast, or both, and saving the images in the memory means.

In the cornea imaging apparatus constructed in accordance with this mode, the task of sorting photographic images by the operator may be rendered unnecessary, or the work entailed appreciably reduced. A specific example of a mode for sorting on the basis of light intensity level would be to save a photographic image to the memory means in the event that the average luminance of the pixels making up the photographic image exceeds a prescribed value. A specific example of a mode for sorting on the basis of contrast would be to save a photographic image to the memory means in the event that the sum of difference in luminance between neighboring pixels exceeds a prescribed value. Specifically, whereas the intensity of reflected light from the epithelium is generally uniform, reflected light from the corneal endothelial cells is brighter towards the center of the cell and darker at the wall so that a clear difference in luminance in apparent, and thus the sum of difference in luminance will be greater. Consequently, by selecting a photographic image with a large sum of difference in luminance, it will be possible to select an image taken of the corneal endothelial cells.

BRIEF DESCRIPTION OF THE DRAWINGS

The foregoing and/or other objects features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
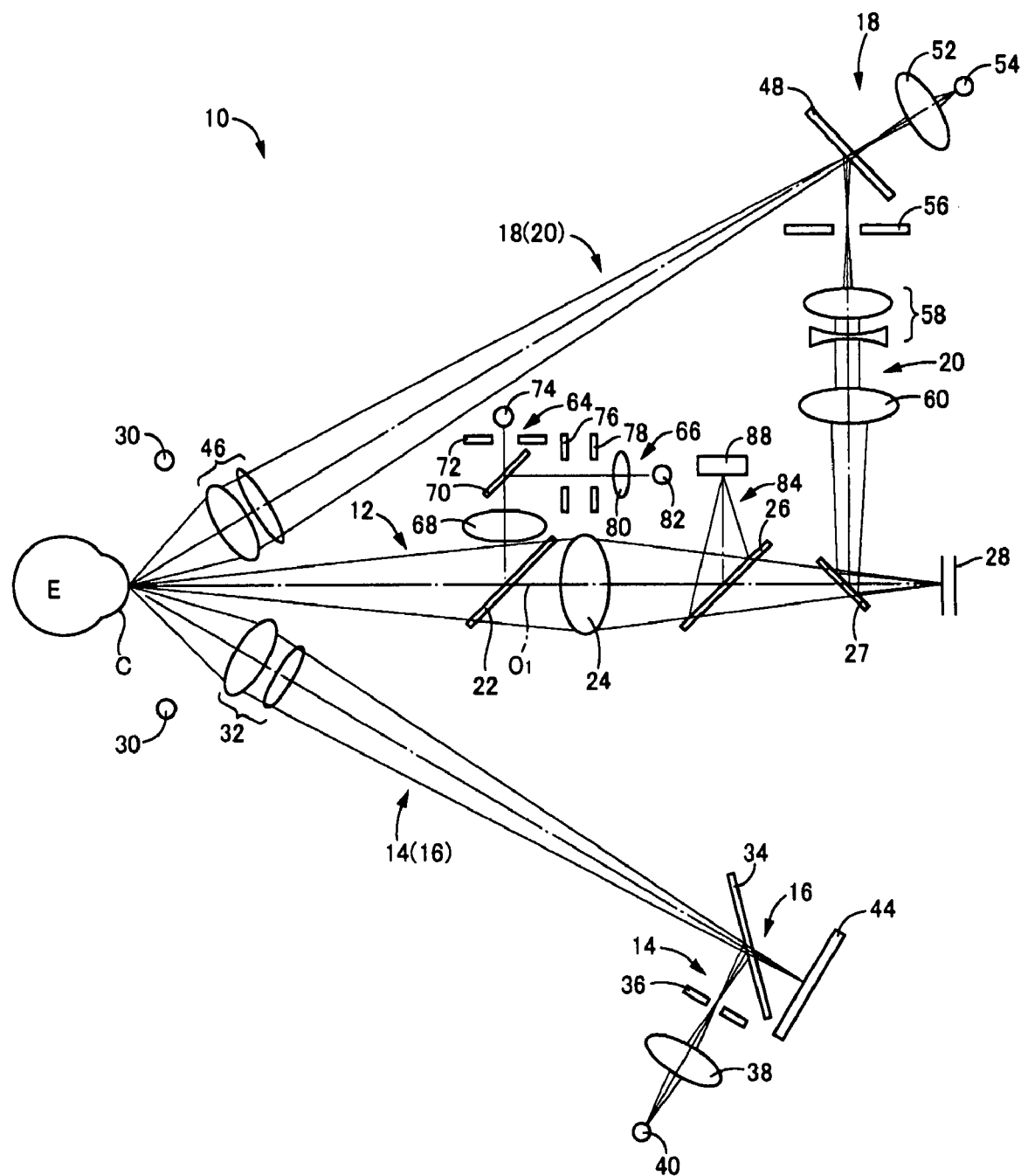
FIG. 1 is a view for explaining an optical system of a cornea imaging apparatus according to a first embodiment of the present invention.

The discussion will refer first to FIG. 1, which depicts an apparatus optical system 10 as one embodiment of the cornea imaging apparatus of the present invention. The apparatus optical system 10 has an imaging illumination optical system 14 and a position sensing optical system 16 situated to one side of an observation optical system 12 for observing the anterior ocular segment of the eye under examination E, and a position detecting illumination optical system 18 and an imaging optical system 20 situated to the other side. In particular, in the present embodiment, the illumination optical system is constituted to include the imaging illumination optical system 14 and the position detecting illumination optical system 18.

The observation optical system 12 is composed, in order from the location nearest the eye under examination E, of a half mirror 22, an objective lens 24, a half mirror 26, a cold mirror 27, and a CCD 28 as the photoelectric element, all positioned on the optical axis O1. A number of observation light sources 30, 30 (two are used in this embodiment) are positioned to the front of the eye under examination E. As the observation light sources 30, 30 it would be possible to use infrared LEDs that emit beams of infrared light, for example. The cold mirror 27 is adapted to transmit infrared light while reflecting visible light, and the reflected light beams emitted by the observation light sources 30, 30 and reflected at the anterior ocular segment of the eye under examination E pass through the objective lens 24 and the cold mirror 27, becoming focused on the CCD 28.

The imaging illumination optical system 14 is composed, in order from the location nearest the eye under examination E, of a projector lens 32, a cold mirror 34, a slit 36, a collecting lens 38, and an imaging light source 40. An LED or the like that emits a beam of visible light is employed as the imaging light source 40 for example. The cold mirror 34 is adapted to transmit infrared light while reflecting visible light. The beam of light emitted by the imaging light source 40 passes through the objective lens 38 and the slit 38, becoming a slit light beam; is reflected by the cold mirror 34 and then passes through the projector lens 32; and is then directed onto the cornea C in the diagonal direction.

The optical axis of the position sensing optical system 16 is partly coincident with the optical axis of the imaging illumination optical system 14; the system is composed, in order from the location nearest the eye under examination E, of the projector lens 32, the cold mirror 34, and a line sensor 44. A beam of light emitted by an observation light source 54, to be described later, and reflected from the cornea C will pass through the projector lens 32 and the cold mirror 34, and be focused on the line sensor 44.

Meanwhile, the position detecting illumination optical system 18 is composed, in order from the location nearest the eye under examination E, of an objective lens 46, a cold mirror 48, a collecting lens 52, and the observation light source 54 as the position-sensing light source. An infrared LED or other infrared light source is preferably used as the observation light source 54. The infrared beam emitted from the observation light source 54 is directed onto the cornea C from the diagonal. The observation light source 54 may also have an arrangement which combines an infrared filter with a halogen lamp, visible light LED, or other visible light source for example. However, the observation light source 54 need not always be an infrared light source; a visible light source such as a halogen lamp or visible light LED could also be used. Where a visible light source is used, the illumination intensity thereof will preferably be lower than the illumination intensity of the imaging light source 40. It will be possible thereby to reduce the burden on the patient when a light beam from the observation light source 54 is directed into the patient's eye during alignment, etc.

The optical axis of the imaging optical system 20 is partly coincident with the optical axis of the position detecting illumination optical system 18; the system is composed, in order from the location nearest the eye under examination E, of the objective lens 46, the cold mirror 48, a slit 56, a variable lens 58, a focusing lens 60, the cold mirror 27, and the CCD 28. A beam of light emitted from the imaging light source 40 and reflected from the cornea C will be reflected by the cold mirror 48 via the objective lens 46; then form a parallel beam by means of the slit 56; be reflected by the cold mirror 27 via the variable lens 58 and the focusing lens 60; and become focused on the CCD 28.

The half mirror 22 provided on the observation optical system 12 constitutes part of a fixation target optical system 64 and an alignment optical system 66.

The fixation target optical system 64 is composed, in order from the location nearest the eye under examination E, of the half mirror 22, a projection lens 68, a half mirror 70, a pinhole plate 72, and a fixation target light source 74. The fixation target light source 74 is an LED or other light source emitting visible light for example. The beam of light emitted from the fixation target light source 74 is transmitted through the pinhole plate 72 and the half mirror 70, then formed into a parallel beam by the projection lens 68 and reflected by the half mirror 22 to direct it into the eye under examination E.

The alignment optical system 66 is composed, in order from the location nearest the eye under examination E, of the half mirror 22, the projection lens 68, the half mirror 70, an aperture 76, a pinhole plate 78, a collecting lens 80, and an alignment light source 82. The alignment light source 82 emits infrared light. The infrared light is collected by the collecting lens 80, passes through the pinhole plate 78, and is guided into the aperture 76. The light passing through the aperture 76 is then reflected from the half mirror 70, formed into a parallel beam by the projection lens 68, and reflected by the half mirror 22 to direct it into the eye under examination E.

The half mirror 26 provided on the observation optical system 12 constitutes part of an alignment detecting optical system 84.

The alignment detecting optical system 84 is composed, in order from the location nearest the eye under examination E, of the half mirror 26, and an alignment detecting sensor 88 capable of detecting position. A light beam emitted by the alignment light source 82 and reflected from the cornea C will be reflected by the half mirror 26, and guided into the alignment detecting sensor 88.

Figure 2:
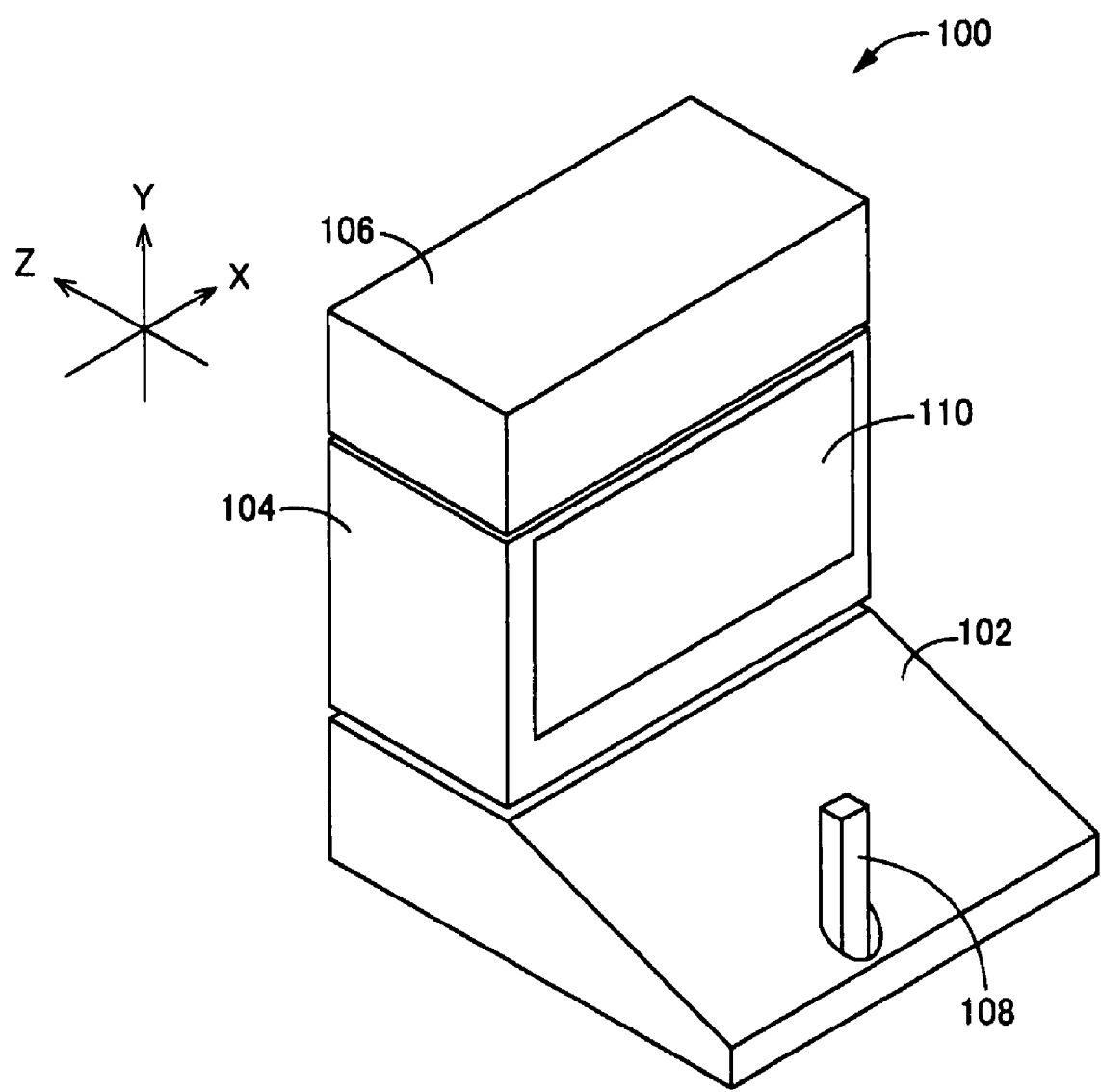
FIG. 2 is a perspective view of the cornea imaging apparatus of the first embodiment.

The apparatus optical system 10 having the structure described above is housed within the cornea imaging apparatus 100 depicted in FIG. 2. The cornea imaging apparatus 100 is provided with a chassis 104 situated on a base 102, and is constituted so that a case 106 can be installed on the chassis 104 so as to be moveable in all directions in a plane and in the vertical direction. The base 102 houses a power supply, and also has a control stick 108; the case 106 can be actuated by operating the control stick 108. The chassis 104 also houses various control circuitry, to be described later, and is provided as well with a display screen 110 composed of a liquid crystal monitor or the like.

Figure 3:
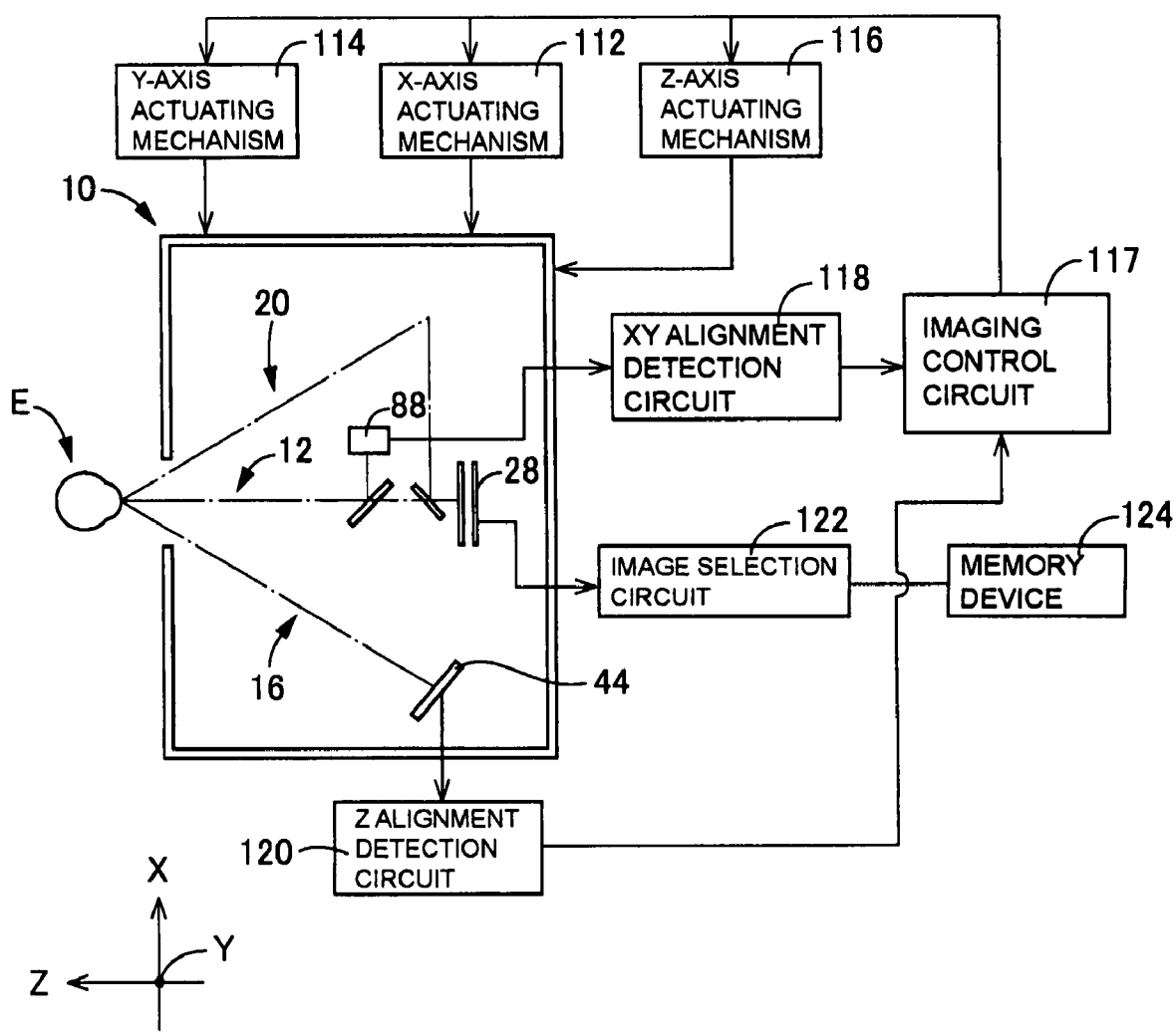
FIG. 3 is a block diagram for explaining a control circuit or the like connected to the optical system of FIG. 1.

As shown in FIG. 3, the cornea imaging apparatus 100 is provided with actuating means for actuating the case 106 in order to move the apparatus optical system 10 in the direction nearer to or further away form the eye under examination E. The actuating means could be composed of a rack and pinion mechanism or the like for example. In the present embodiment, it is furnished with an X-axis actuating mechanism 112 for actuating the apparatus optical system 10 in the vertical direction (X direction) in FIG. 3; a Y-axis actuating mechanism 114 for actuating the optical system perpendicular to the plane of the paper (Y direction) in FIG. 3; and a Z-axis actuating mechanism 116 for actuating the optical system sideways (Z direction) in FIG. 3.

The cornea imaging apparatus 100 is also provided with an imaging control circuit 117 as imaging operation control means for controlling the imaging operation of the cornea by the apparatus optical system 10. The X-axis actuating mechanism 112, Y-axis actuating mechanism 114, and Z-axis actuating mechanism 116 are respectively connected to the imaging control circuit 117, so as to be actuatable on the basis of drive signals from the imaging control circuit 117. The alignment detecting sensor 88 is connected to an XY alignment detection circuit 118, and this alignment detection circuit 118 is connected to the imaging control circuit 117. The line sensor 44 is connected to a Z alignment detection circuit 120, and this Z alignment detection circuit 120 is connected to the imaging control circuit 117. Thus, sensor information from the alignment detecting sensor 88 and the line sensor 44 is input to the imaging control circuit 117. While not shown in the drawing, the imaging control circuit 117 is also connected to the illumination light sources 30, 40, 54, 74, and 82, and can control emission of light from these elements.

The cornea imaging apparatus 100 is also furnished with an image selection circuit 122 for inputting of images captured by the CCD 28 and for sorting the images; and with a memory device 124 as memory means for saving images selected by the image selection circuit 122.

Next, an overview of the procedure for imaging the corneal endothelium, executed by the imaging control circuit 117 in the cornea imaging apparatus 100, will be described in the following order.

Figure 5:
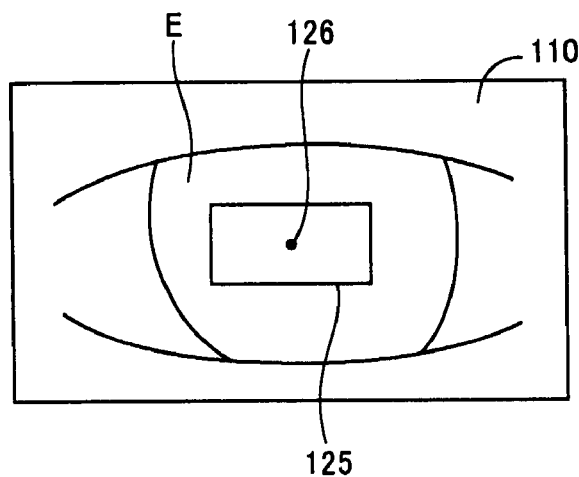
FIG. 5 is a schematic illustration for explaining an anterior ocular segment displayed on a display screen.

First, in S1, positioning of the apparatus optical system 10 in the X and Y directions (XY alignment) is performed. During this XY alignment process, fixation target light emitted from the fixation target light source 74 is directed into the eye under examination E. Then, with the patient's vision fixated on the fixation target light, the direction of the optical axis of the eye under examination E can be aligned with the direction of the optical axis O1 of the observation optical system 12. Under this condition, light is emitted from the observation light sources 30, 30, and the beam of light reflected from the anterior ocular segment of the eye under examination E is guided onto the CCD 28. By means of this procedure, the anterior ocular segment of the eye under examination E is displayed on the display screen 110, as shown in FIG. 5.

An alignment pattern 125 having a rectangular frame pattern, generated by means of a superimposed signal for example, is shown superimposed on the eye under examination E, on the display screen 110. At the same time, the beam of light emitted from the alignment light source 82 is reflected from the anterior ocular segment of the eye under examination E and guided onto the CCD 28, and is thereby displayed on the display screen 110 as alignment light 126 having a dot pattern. By operating the control stick 108, the operator then actuates the apparatus optical system 10 to adjust the position of the apparatus optical system 10 so that the alignment light 126 is positioned inside the frame of the alignment pattern 125.

A portion of the light beam emitted from the alignment light source 82 and reflected from the anterior ocular segment of the eye under examination E is reflected by the half mirror 26 and guided into the alignment detecting sensor 88. The burden on the patient is reduced by directing a beam of infrared light, which is not noticeable to the patient, from the alignment light source 82 into the patient's eye. When the alignment light 126 enters inside the frame of the alignment pattern 125, the alignment detecting sensor 88 can detect the position of the alignment light 126 in the X direction and in the Y direction. The X direction position and the Y direction position are then input to the XY alignment detection circuit 118. The XY alignment detection circuit 118, on the basis of the X direction position information, actuates the X-axis actuating mechanism 112 so as to bring the optical axis O1 of the observation optical system 10 into proximity with the optical axis of the eye under examination E. On the basis of the Y direction position information, actuates the Y-axis actuating mechanism 114 so as to bring the optical axis O1 of the observation optical system 10 into proximity with the optical axis of the eye under examination E. By means of this operation, the apparatus optical system 10 is aligned in the X and Y directions with respect to the eye under examination E. As will be discussed later, this XY alignment is carried out at suitable timing during the imaging process. In particular, in the present embodiment, the alignment light source 81 and the observation light sources 30, 30 flash alternately for brief intervals, and detection by the alignment detection sensor 88 is carried out so as to coincide with the timing of light-up of the alignment light source 81. Thus, the infrared light beams from the observation light sources 30, 30 will be unaffected during XY alignment. Moreover, since flashing of the alignment light source 81 and the observation light sources 30, 30 is carried out at faster speed than the speed of conversion to a photoreception signal in the CCD 28, flashing of the two light sources 82, 30 is not noticeable on the display screen 110 which outputs the photoreception signal from the CCD 28, so both of the light sources 82, 30 appear to be lit continuously.

Next, in S2, the Z-axis actuating mechanism 116 is actuated, and the apparatus optical system 10 is advanced in the direction nearer to the eye under examination E. In the present embodiment, in the above manner, S2 and the Z-axis actuating mechanism 116 are included in the constitution of the pre-imaging process advancing control means or devices. The observation light source 54 is then caused to emit light, and the beam of infrared light emitted from the observation light source 54 is directed in the diagonal direction onto the cornea C of the eye under examination E, while the light beam reflected from the cornea C is received by the line sensor 44. In particular, in the present embodiment, there is less of a burden on the patient, since the light beam emitted from the observation light source 54 is a beam of infrared light.

Figure 6:
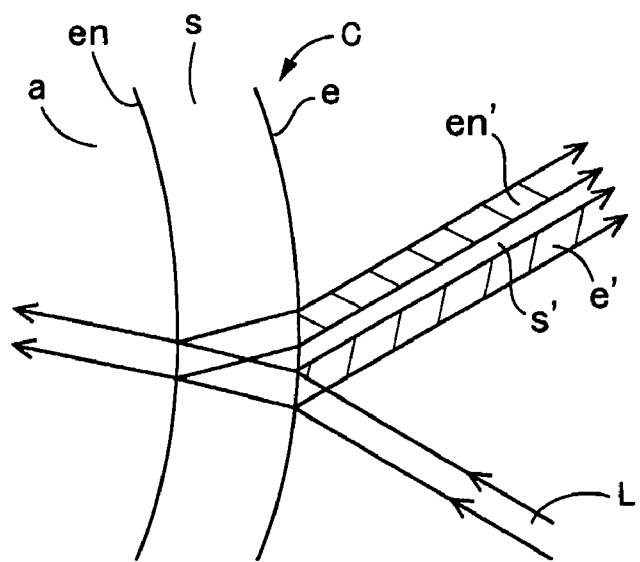
FIG. 6 is an illustration for explaining infrared beam reflected by various layers of cornea.

The beam of infrared light emitted from the observation light source 54 will be reflected with varying reflection intensity by the various layers of the cornea C, i.e. the epithelial cells, the parenchyma, and the endothelium of the cornea C. As depicted in simplified form in FIG. 6, the infrared beam L from the observation light source 54 is first reflected by the epithelial cells e which constitute the boundary between the air and the cornea C. A portion of the beam passing through the epithelial cells e is reflected by the parenchyma s and the endothelium en. The reflected beam e' reflected by the epithelial cells e has the highest light intensity, while the light intensity of the reflected beam en' reflected by the endothelium en is relatively lower, and the light intensity of the reflected beam s' reflected by the parenchyma s is lowest of all. Since the anterior chamber a is filled with aqueous humor, there is substantially no reflection of the infrared beam L by the anterior chamber a.

Figure 7:
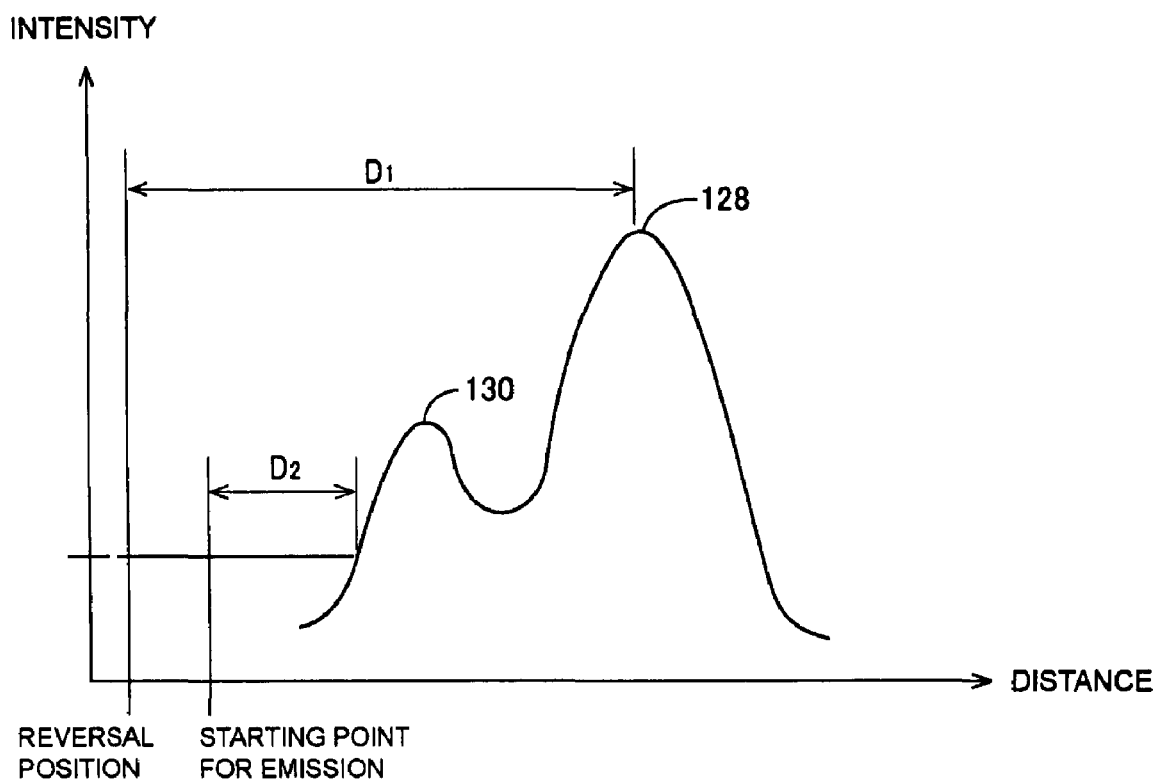
FIG. 7 is a graph demonstrating a light intensity distribution of reflected beams detected by light intensity detecting means.

These reflected beams are detected by the line sensor 44. The line sensor 44 will detect a light intensity distribution like that of FIG. 7. In FIG. 7, the first peak 128 with the highest intensity represents reflected light from the epithelium. The second peak 130 with the next highest order of intensity represents reflected light from the endothelium. The imaging control circuit 117 then actuates the Z-axis actuating mechanism 116 and advances the apparatus optical system 10 the direction nearer to the cornea C, by a prescribed distance D1 from the position of the epithelium detected by the line sensor 44, which distance has been specified taking into consideration variability in physiological cornea thickness of the human eye. The distance of movement from the epithelium is appropriately established with a range of 1000 to 1500 μm, for example. The focal position of the imaging optical system 20 in the apparatus optical system 10 is thereby positioned rearward from the endothelial cells of the cornea C. This position located rearward of the epithelium by distance D1 is designated as the reversal position of the apparatus optical system 10.

Figure 8:
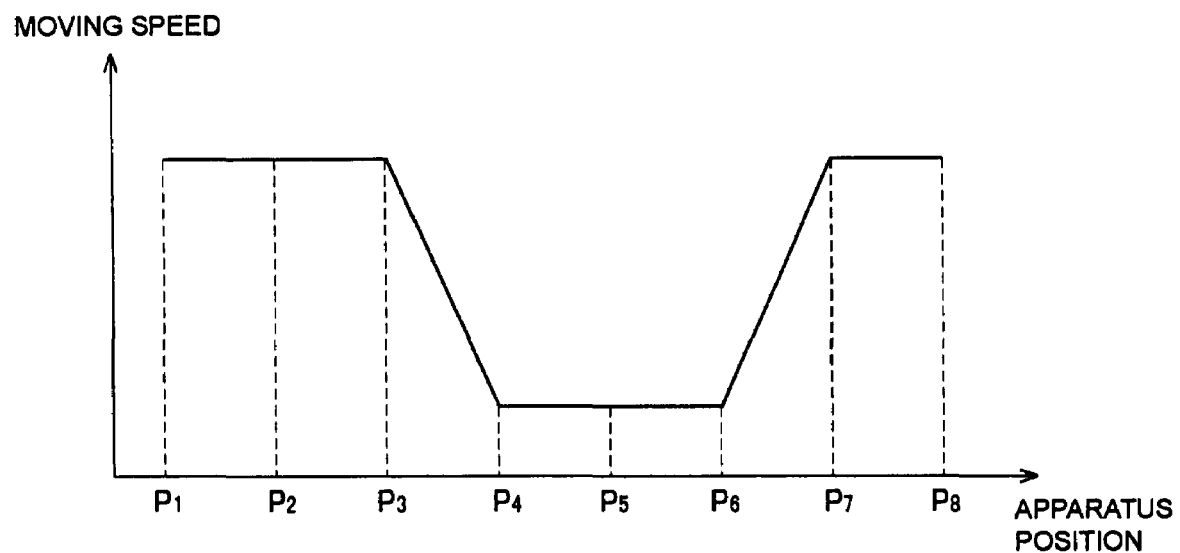
FIG. 8 is a graph demonstrating a change in moving speed of the apparatus optical system.

Next, once the apparatus optical system 10 has been positioned at the reversal position, in S3 the Z-axis actuating mechanism 116 is actuated in the opposite direction, whereby the apparatus optical system 10 retracts in the direction away from the eye under examination E on the Z axis. In the present embodiment, in the above manner, S3 and the Z-axis actuating mechanism 116 are included in the constitution of the reversal operation control means or device and of the imaging process retracting control means. The apparatus optical system 10 initiates the retracting operation starting from the reversal position, and the retraction speed is varied until the imaging process terminates. FIG. 8 depicts the change in moving speed of the apparatus optical system 10 during the retracting operation.

First, as mentioned earlier, the apparatus optical system 10 initiates the retracting operation starting from the reversal position (P1 in FIG. 8). The retracting operation is carried out at relatively high speed, from 500 μm to 3000 μm/sec, more preferably around 2000 μm/sec. Then, in S4, starting from the point in time that the apparatus optical system 10 reaches a position (P2 in FIG. 8) located a prescribed distance D2 (see FIG. 7) back from the endothelium cell position, the observation light sources 30, 30 are extinguished and emission of light by the imaging light source 40 begins. In the present embodiment, the prescribed distance D2 from the epithelial cells is a distance away from the position of a prescribed threshold value at which the light intensity distribution detected by the line sensor 44 is slightly lower than the second peak 130. As a specific example of the prescribed distance D2, although a value with a certain degree of latitude is preferred so that the endothelial cells can be ascertained reliably in consideration of the detection accuracy of the line sensor 44 and of shift of position of the eye under examination E, it is preferable to employ as the prescribed distance D2 a value within a range of between 200 and 500 μm, since greater prescribed distance D2 is associated with longer emission time by the imaging light source 40 and with increased burden on the patient. The imaging light source 40 is designed to emit light while flashing at a prescribed brief interval, with the XY alignment in S1 being carried out simultaneously with the timing of extinguishment of the imaging light source 40.

Then, while retracting the apparatus optical system 10 at relatively high speed, in S5, deceleration of the apparatus optical system 10 is initiated at a point in time (P3 in FIG. 8) at which the reflected light from the endothelial cells is detected by the CCD 28. Detection of reflected light from the endothelial cells in S5 is accomplished in the manner shown in FIG. 9, for example, through a determination that reflected light from the endothelial cells has been detected, based on the number of pixels having luminance above a prescribed value from among luminance values of pixels situated on one or more appropriate horizontal lines (five in the present embodiment) 11 to 15, in the image 132 captured by the CCD 28. In the present embodiment, luminance of the pixels in the image 132 is detected in 255 levels ranging from a luminance value of 1 to a luminance value of 255 (with the luminance value of 1 being the darkest and the luminance value of 255 being the brightest); in consideration of variability in reflected light from the endothelium, luminance of pixels located on the five horizontal lines 11 to 15 of the image 132 is detected. Then, numbers of pixels with luminance values of between 25 and 255 among the pixels on the horizontal lines 11 to 15 is counted. Luminance values of between 25 and 255 represent light intensity clearly visible to the naked eye as reflected light. Then, the average value of the numbers of counted pixels in the horizontal lines 11 to 15, or the maximum value of the numbers of counted pixels in the horizontal lines 11 to 15, is converted to distance on the endothelium, and a location (P3 in FIG. 8) corresponding to the intensity of reflected light at approximately 30 μm is designated as the starting point for deceleration.

Then, the deceleration operation in S5 is initiated, as well as initiating continuous imaging of the endothelium detected by the CCD 28, in S6, which are cooperate to provide a continuous imaging means or devices. This continuous imaging is carried out by inputting to the image selection circuit 122 photographic images (images) received by the CCD 28 at prescribed time intervals (e.g. 1/30 of a second). By means of this process, a series of corneal images taken at different times and positions is input to the image selection circuit 122. Then, in conjunction with this continuous imaging, the image selection circuit 122 performs sorting of input images and saving them to the memory device 124. In the present embodiment, in the above manner, S6 and the image selection circuit 122 are included in the constitution of the continuous imaging control means or device and of the image selecting means or device.

Figure 9:
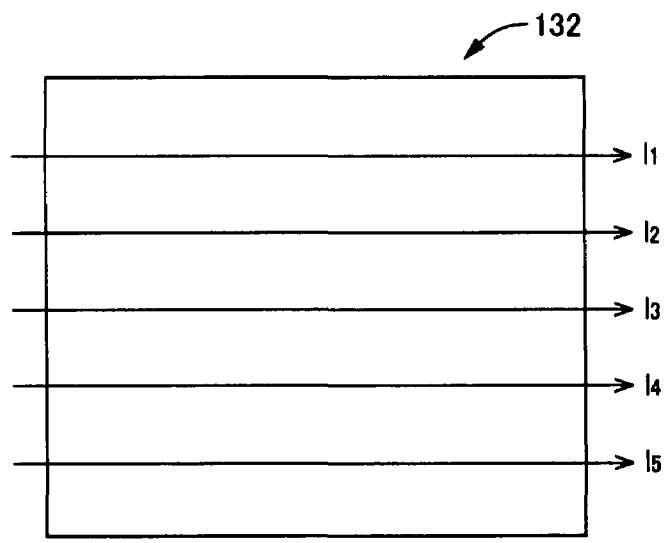
FIG. 9 is a schematic diagram for explaining a method of detecting reflected light from a corneal endothelium, and a method of selecting a photographic image.
Figure 10:
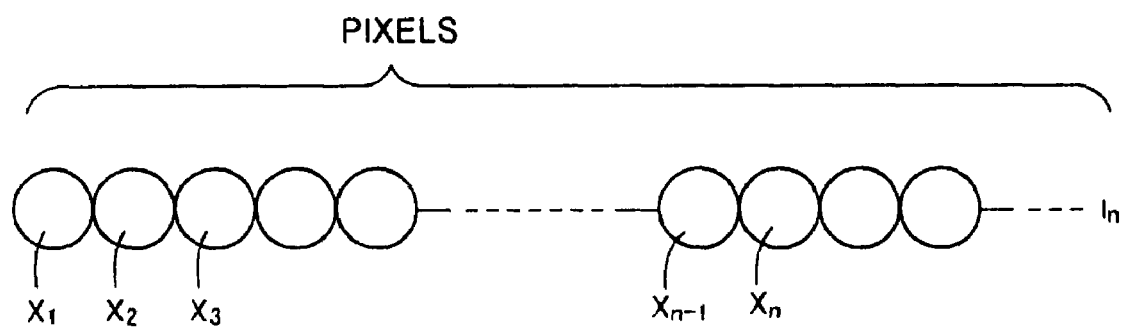
FIG. 10 is an illustration for explaining a method of selecting a photographic image.

FIGS. 9 and 10 show an exemplary method for sorting images in the image selection circuit 122. First, in a manner analogous to detection of the endothelial cells in S5 described earlier, luminance is detected for pixels on one or more horizontal lines (five in the present embodiment) 11 to 15 in the image 132 acquired by the CCD 28, as shown in FIG. 9.

$$\Sigma |X_n - X_{n-1}| \qquad \text{[Expression 1]}$$

Then, as shown in FIG. 10 and Expression 1, for each of the lines 11 to 15, (i) the absolute value of the luminance differential of neighboring pixels and (ii) the total luminance differential is calculated for the pixels (X1 to Xn) of the acquired horizontal lines 11 to 15.

Figure 11:
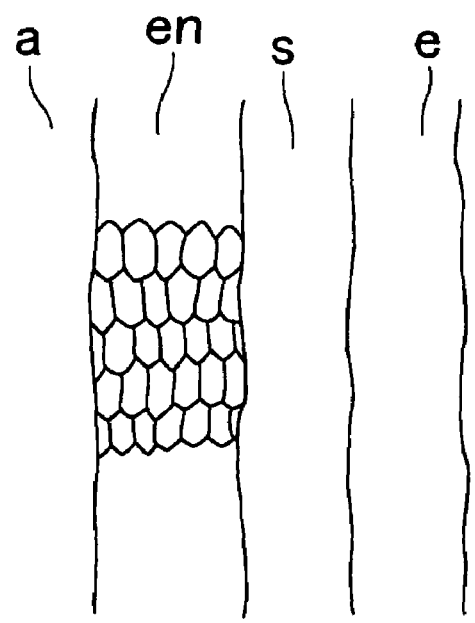
FIG. 11 is an illustration for explaining a structure of a variety of layers of a cornea.

The average value of the total luminance differential calculated on the basis of Expression 1 for each of the horizontal lines 11 to 15 is then derived. The larger this value is, the wider the range of the endothelial cells captured in the image is recognized to be. Specifically, as shown in simplified form in FIG. 11 and in FIG. 6 discussed previously, an image taken of the anterior chamber a will be a dark image overall due to the fact that the illuminating light beams are transmitted through the aqueous humor, with substantially no reflected light beams obtained. An image taken of the parenchyma s will also be a dark image overall, due to the fact that the parenchyma s is transparent and, like the anterior chamber a, transmits the illuminating light beams. At the epithelial layer, there is considerable reflected light intensity, and thus an image thereof will be bright overall. Consequently, differences in luminance values of neighboring pixels will be minimal in images of these regions. In the endothelium en on the other hand, contrast between the center portions and the cell walls of the endothelial cells is clearly apparent and there are large luminance differentials among neighboring pixels, so an image taken of the endothelial cells over a wide range will contain a large total luminance differential. Accordingly, by saving to the memory device 124 only those images whose average total luminance differential calculated for the horizontal lines 11 to 15 exceeds a prescribed threshold value, it will be possible to select only images that effectively capture the endothelial cells.

In particular, in the present embodiment, if prior to making the aforementioned determination a series of consecutive pixels having luminance values of 240 or above is found to be present over a range of between about 50 μm and 100 μm in prescribed horizontal lines (e.g. the aforementioned horizontal lines 11 to 15), the image will be excluded. Specifically, where part of the epithelium is captured in an image, a considerable luminance value differential will be produced on the boundary line between the epithelium and the parenchyma. Thus, in the event that the total luminance value differential in the endothelium should be low owing, for example, to incorrect focal position of the endothelial cells (blurred focus), there is a risk that the boundary line with the parenchyma will produce a large luminance value differential, posing a risk that the image will be erroneously selected as one capturing the endothelium. Consequently, the system is designed to enable exclusion of images that capture part of the epithelium, by using the decision criterion mentioned above.

Next, in S5 the deceleration operation is initiated, and at the point in time that relatively low speed, discussed later, is reached (P4 in FIG. 8), the apparatus optical system 10 is retracted at this constant, relatively low speed. Also, at the point in time that deceleration is complete, continuous imaging and image sorting are carried out in S6, over a prescribed range (between P4 and P6 in FIG. 8). The focal position of the endothelial cells (P5 in FIG. 8) is assumed to lie within the range P4 and P6.

Here, the relatively low speed of movement when deceleration is complete in S5 will be determined with consideration to the range over which continuous imaging will be carried out while moving at low speed (between P4 and P6 in FIG. 8), the image capture time of the CCD 28, the number of frames, and so on. For example, in consideration of possible slight movement of the eye under examination E, a range of 200 µm or more could be employed as the range for continuous imaging at low speed. Assuming a CCD 28 image capture time of 1/30 second per frame and a continuous imaging range of 200 µm, a speed of 600 µm/sec would be necessary when taking 10 frames, 300 µm/sec would be necessary when taking 20 frames, 200 µm/sec would be necessary when taking 30 frames, 150 µm/sec would be necessary when taking 40 frames, and 100 µm/sec would be necessary when taking 50 frames. Consequently, it will be preferable to employ a speed of between 100 and 300 µm/sec in order to reliably acquire images of the endothelium through continuous imaging. In this way, according to the present embodiment, the number of frames taken through continuous imaging is adjusted by varying the speed of movement of the apparatus optical system 10, with the image capture time of the CCD 28 generally unchanging; however it would also be acceptable, for example, to adjust the number of frames by varying the interval of image capture time of the CCD 28 on the basis of reflected light from the endothelium in S5, with the speed of movement of the apparatus optical system 10 constant; or to control both the speed of movement and the capture time.

Next, in S7, at a point in time (P6 in FIG. 8) that the retracting movement has taken place over a prescribed distance (e.g. 200 µm in the present embodiment) from the starting position of low-speed movement and continuous imaging (P4 in FIG. 8), acceleration will be initiated and the apparatus optical system 10 will be accelerated up to the speed at which it was moved prior to initiating deceleration. The criterion for determining the acceleration start position is not limited to distance of movement. For example, in accordance with a method similar to the procedure for detecting reflected light from the cornea in S5 discussed previously, acceleration could be initiated at a stage where reflected light from the cornea is no longer detected; acceleration could be initiated following a prescribed time interval from initiation of imaging; or some appropriate combination of these could be employed.

Once the apparatus optical system 10 has been accelerated and reached relatively high speed equal to that prior to initiating deceleration (P7 in FIG. 8), in S8, the system is retracted by about 100 µm for example, in consideration of possible slight movement of the eye under examination E; subsequently, the retraction operation is halted, the imaging light source 40 is extinguished, and the imaging process terminates (P8 in FIG. 8).

Figure 12:
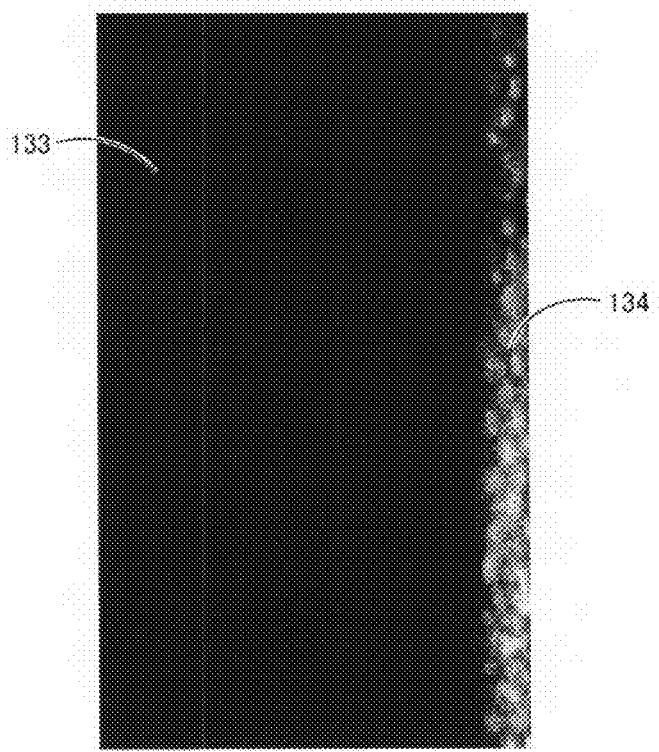
FIG. 12 is an image of a corneal endothelium at a point P3 in FIG. 8.
Figure 13:
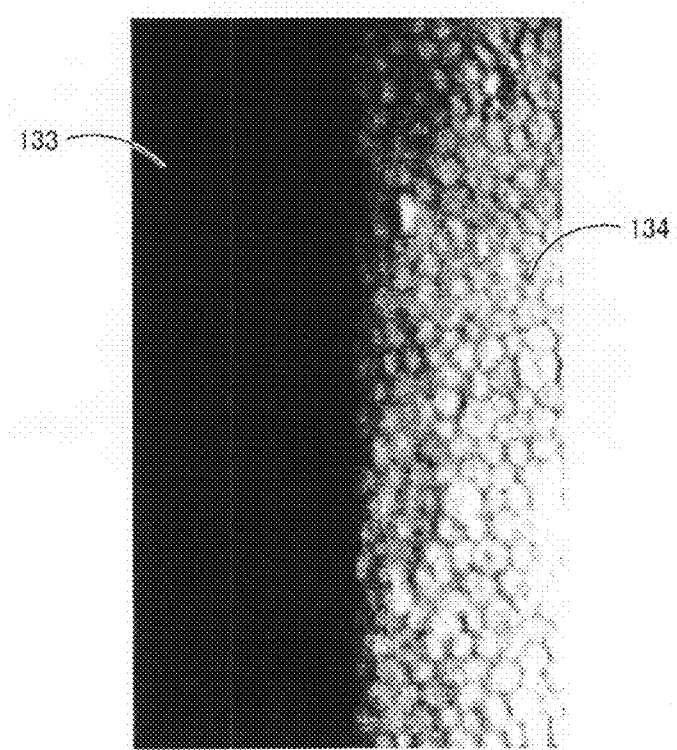
FIG. 13 is an image of a corneal endothelium at a point P4 in FIG. 8.
Figure 14:
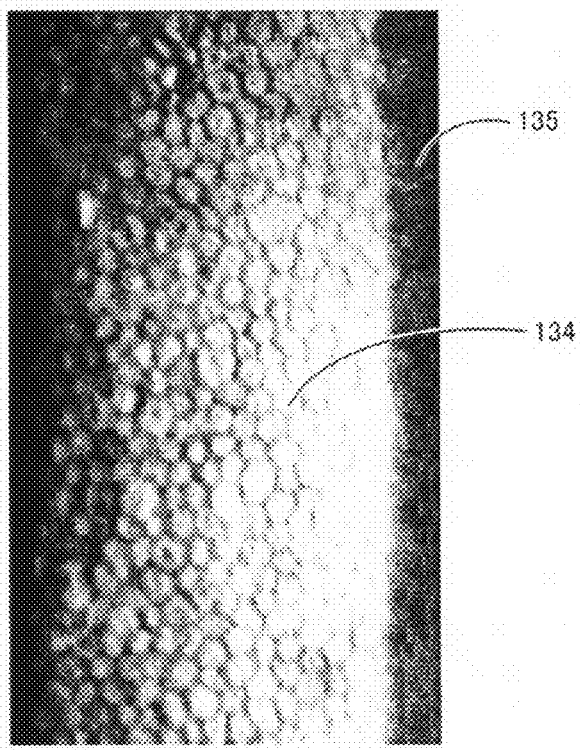
FIG. 14 is an image of a corneal endothelium at a point P5 in FIG. 8.
Figure 15:
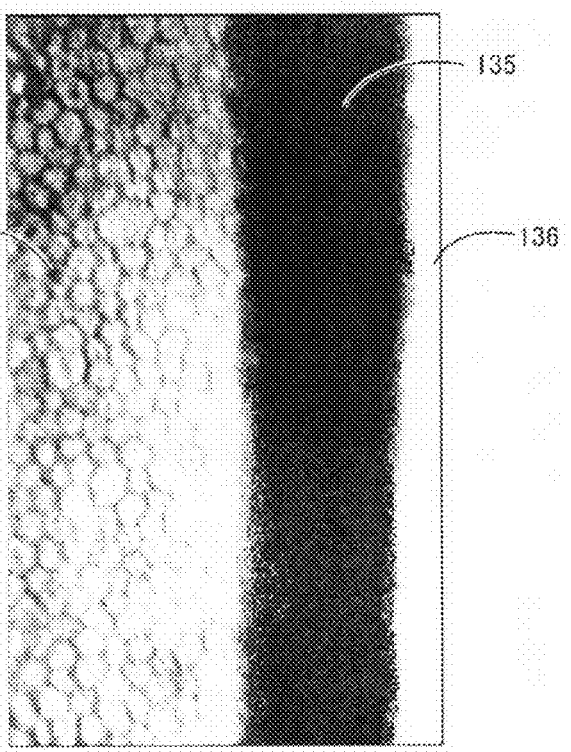
FIG. 15 is an image of a corneal endothelium at a point P6 in FIG. 8.
Figure 16:
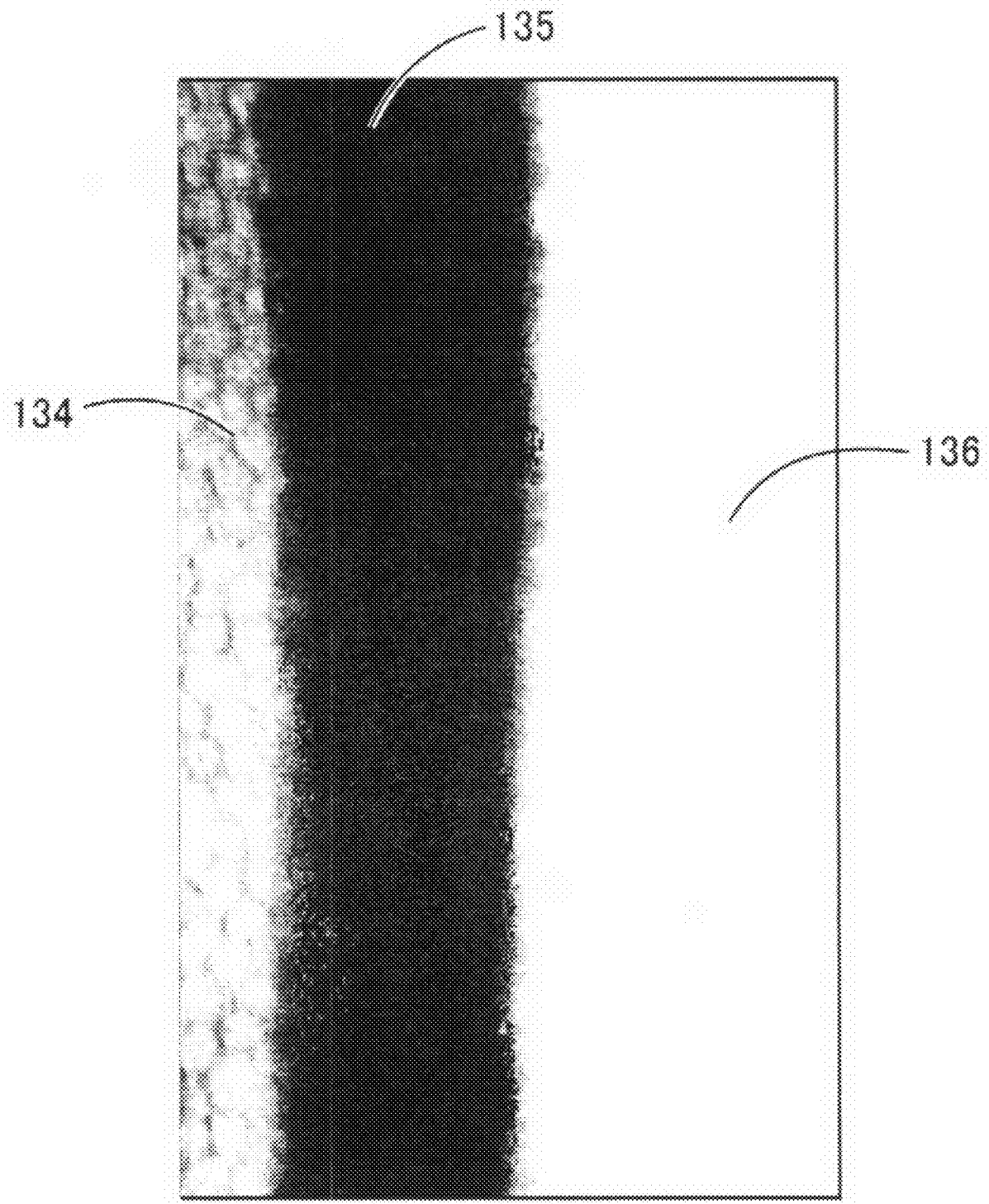
FIG. 16 is an image of a corneal endothelium at a point P6 in FIG. 8.

FIGS. 12 to 16 depict images of the endothelial cells taken at various positions in the course of retraction of the apparatus optical system 10. First, FIG. 12 is an image of the endothelial cells taken in proximity to the position where reflected light from the endothelium is received by the CCD 28 (in proximity to P3 in FIG. 8). At this position, an anterior ocular equivalent segment 133 fills virtually the entire area of the screen, with a small slice of endothelial cells 134 discernible at the right edge of the screen. Since illuminating light is transmitted by the anterior ocular segment with substantially no reflection, the anterior ocular equivalent segment 133 appears dark. FIG. 13 is an image of the endothelial cells taken in proximity to the position where low-speed operation is initiated (in proximity to P4 in FIG. 8). Compared with the vicinity of P3 (FIG. 12), at this position the left edge of the endothelial cells 134 has shifted to a more rightward position in the image, and the endothelial cells 134 appear larger in the image. FIG. 14 is an image of the endothelial cells taken in proximity to the focal position of the endothelial cells (in proximity to P5 in FIG. 8). The endothelial cells 134 appear largest at this position. At the right edge of the screen, the parenchyma 135 appears darker than the endothelial cells 134. FIG. 15 is an image of the endothelial cells taken in proximity to [the position] where low-speed operation of the apparatus optical system 10 concludes (in proximity to P6 in FIG. 8). Compared with the vicinity of P5 (FIG. 14), at this position the right edge of the endothelial cells 134 has shifted to a more leftward position in the image, the endothelial cells 134 appear smaller in the image, and the epithelium 136 is visible at the right edge of the screen. FIG. 16 is an image of the endothelial cells taken in proximity to the position where acceleration subsequent to low-speed operation of the apparatus optical system 10 concludes (in proximity to P7 in FIG. 8). At this position, the endothelial cells 134 are only slightly visible at the left edge of the image, with the epithelium 136 taking up most of the image. As [the optical system] travels from a position to the rear of the endothelium towards the focal position of the endothelium in this way, the endothelial cells appear progressively larger, appearing largest at the focal position of the endothelium. Then, with further retraction past the focal position of the endothelium, the cells appear progressively smaller.

In the cornea imaging apparatus 100 having the construction described above, as the apparatus optical system 10 travels from the rear of the cornea C the position of the endothelial cells is detected by means of reflected light from the rear edge of the endothelium of the cornea C, whereby it is possible to correctly detect the position of the endothelial cells free from the effects of reflected light from the parenchyma etc. Since the reflected light from the endothelial cells is light that is actually reflected from the eye under examination E, the position of the endothelial cells can be detected correctly, irrespective of individual differences in corneal thickness among patients. Consequently, imaging of endothelial cells can be carried out reliably.

Moreover, in the present embodiment, the apparatus optical system 10 moves at relatively high speed until reaching the endothelial cells, whereby the time required for imaging can be reduced, and the burden on the patient can be alleviated.

Furthermore, in the present embodiment, since sorting of captured images is performed by the image selection circuit 122, only images captured under good conditions will be handled. It is possible thereby to reduce the labor required to sort images of multiple frames taken by means of continuous imaging and so on, making the task more efficient.

While the present invention has been described in detail in its presently preferred embodiment, for illustrative purpose only, it is to be understood that the invention is by no means limited to the details of the illustrated embodiment, but may be otherwise embodied.

For example, the apparatus optical system 10 described above is merely exemplary, and the constitution and placement locations of the lenses and slits making up the optical systems are not limited to the constitution described above. For example, whereas in the preceding embodiment a cold mirror 27 is positioned on the optical axis O1 of the observation optical system 12, it would be acceptable for example to replace the cold mirror 27 with a mirror producing total reflection of the received light beam and positioned at a location away from the optical axis O1, from where it reflects the light beam from the imaging light source 40 onto the CCD 28. It is not always necessary for the observation light sources 30, 30 to be infrared light sources; visible light sources could be used as well. Alternatively, a mirror producing total reflection of the received light beam could be positioned moveably on the optical axis O1 so as to be alternately switchable between a state in which the mirror guides the light beam of the observation optical system 12 onto the CCD 28 while blocking the light beam of the observation optical system 12, and a state in which the mirror moves to a location away from the optical axis O1 of the observation optical system 12 and guides the light beam of the observation optical system 12 onto the CCD 28. Also, the positions of the observation light source 54 and the line sensor 44 could be switched.

Figure 4:
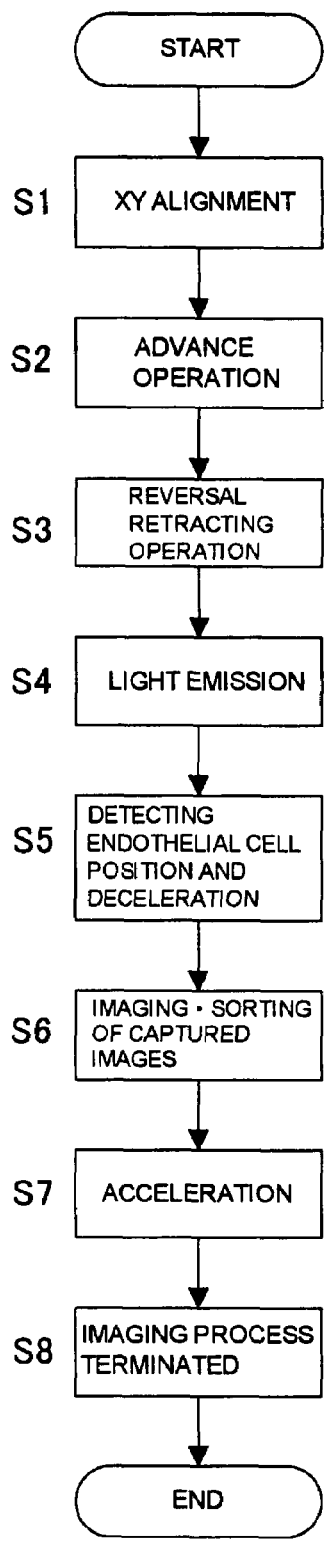
FIG. 4 is a flow chart demonstrating imaging process executed by the cornea imaging apparatus.

The line sensor 44 in the preceding embodiment is not essential. It would be possible to instead establish the reversal location at a position advanced by a prescribed distance towards the eye under examination E after the position of the endothelium has been detected by the CCD 28; and to then initiate the retraction operation from this reversal location, for example. Specifically, light from the imaging light source 40 reflected from the eye under examination E will be received by the CDD 28 as the apparatus optical system 10 advances towards the eye under examination E. The apparatus optical system 10 continues to advance until reflected light from the endothelium is detected by the CCD 28. In this instance, detection can be carried out in a generally similar manner to detection of reflected light from endothelial cells (FIG. 4, S5) in the preceding embodiment, for example. Specifically, luminance values are acquired for pixels on a prescribed number of lines (e.g. five) from an image received by the CCD 28; and at a point in time that the number of pixels having luminance above a prescribed threshold value equivalent to the reflected image from the endothelium exceeds a prescribed number, it will be determined that reflected light from the endothelium has been detected.

Next, taking corneal thickness into consideration, the apparatus optical system 10 advances further beyond the position at which reflected light from the endothelium was detected, by a prescribed distance enabling a position to the rear of the endothelium to be reached (e.g. distance D1 shown in FIG. 7 in the preceding embodiment). By so doing, the apparatus optical system 10 can be positioned at generally the same position as the reversal initiation position in the preceding embodiment. Then, from this position the reversal operation is initiated and scanning begins. In this embodiment, in order to enable detection of reflected light from the endothelium, the imaging light source 40 will begin to emit light from the outset of the advancing operation, and will therefore already be lit when the reversal operation begins.

An advantage of this embodiment is that accurate imaging of endothelial cells can be accomplished with a simpler design, since the line sensor 44 is unnecessary. Moreover, the cornea imaging apparatus can be made more compact due to the simpler design.

What is claimed is:

1. A cornea imaging apparatus comprising:
   an illumination optical system having an illumination source for directing a slit light beam on a diagonal into an eye under examination;
   an imaging optical system having a photoelectric element for receiving a reflected light beam produced by reflection of the slit light beam from a cornea of the eye under examination, and for imaging the cornea;
   actuating means for moving the illumination optical system and the imaging optical system in totality in a direction nearer to or further from the eye under examination to bring about focusing;
   imaging process retracting control means for controlling the actuating means during an imaging operation by the imaging optical system, to retract the illumination optical system and the imaging optical system in a direction away from the eye under examination in a cross direction of the eye under examination;
   continuous imaging means for taking multiple images of the cornea at different times and positions by the photoelectric element of the imaging optical system during a retracting operation by the imaging process retracting control means; and
   imaging operation control means for controlling imaging operation status of the cornea by the continuous imaging means during the retracting operation by the imaging process retracting control means, with reference to a photoreception signal of reflected light from the cornea of the eye under examination.

2. The cornea imaging apparatus according to claim 1, wherein the illumination sources of the illumination optical system comprises an imaging light source for imaging the cornea by means of guiding, into the photoelectric element of the imaging optical system, reflected light that has been directed into the eye under examination and reflected from the cornea; and with an output signal by the photoelectric element of reflected light produced by reflection by the cornea of an illuminating light beam from the imaging light source utilized as the photoreception signal, a cornea imaging operation status is controlled in the imaging operation control means on the basis of the output signal of the photoelectric element.

3. The cornea imaging apparatus according to claim 2, wherein with the output signal by the photoelectric element utilized as the photoreception signal, the cornea imaging operation status is controlled in the imaging operation control means on the basis of the output signal of the photoelectric element by means of controlled modification of a speed of the retracting operation by the imaging process retracting control means.

4. The cornea imaging apparatus according to claim 2, wherein with the output signal by the photoelectric element utilized as the photoreception signal, the cornea imaging operation status is controlled in the imaging operation control means on the basis of the output signal of the photoelectric element by means of controlled modification of a continuous imaging time interval of the cornea by the continuous imaging means.

5. The cornea imaging apparatus according to claim 1, wherein a position-sensing light source is employed as one of the illumination sources of the illumination optical system, separate from an imaging light source used for imaging the cornea by means of guiding, into the photoelectric element of the imaging optical system, reflected light that has been directed into the eye under examination and reflected from the cornea; a line sensor for receiving the reflected light produced by reflection by the cornea of an illuminating light beam is employed as the position-sensing light source; and with an output signal by the line sensor as utilized as the photoreception signal, the cornea imaging operation status is controlled in the imaging operation control means on the basis of the output signal of the line sensor.

6. The cornea imaging apparatus according to claim 5, wherein in the imaging operation control means, emission of light by the imaging light source and a cornea imaging operation by the continuous imaging means are controlled so as to be respectively initiated on a condition that reflected light from the cornea has been verified on the basis of the output signal of the line sensor.

7. The cornea imaging apparatus according to claim 6, wherein in the imaging operation control means, a detection level of an output signal is set to one corresponding to a prescribed intensity lower than that of an output signal corresponding to reflected light intensity at a focal location from a corneal endothelium detected by the line sensor.

8. The cornea imaging apparatus according to claim 1, further comprising: pre-imaging process advancing control means for controlling the actuating means and advancing the illumination optical system and the imaging optical system in a direction closer to the eye under examination in the cross direction of the eye under examination, prior to the retracting operation by the imaging process retracting control means during the imaging operation; and reversal operation control means for controlling reversal of a direction of movement from advancing operation by the pre-imaging process advancing control means to the retracting operation by the imaging process retracting control means, on the basis of the photoreception signal of reflected light from the cornea of the eye under examination.

9. The cornea imaging apparatus according to claim 8, wherein a position-sensing light source is employed as one of the illumination sources of the illumination optical system, separate from an imaging light source used for imaging the cornea by means of guiding, into the photoelectric element of the imaging optical system, reflected light that has been directed into the eye under examination and reflected from the cornea; a line sensor for receiving the reflected light produced by reflection by the cornea of the illuminating light beam is employed as the position-sensing light source; an output signal of the line sensor is used as the photoreception signal of reflected light from the cornea of the eye under examination; and on the basis of the output signal of the line sensor, the direction of movement during the advancing operation by the pre-imaging process advancing control means is reversed by the reversal operation control means, at a reversal position established to a rear of an endothelium focal position.

10. The cornea imaging apparatus according to claim 1, wherein in the imaging operation control means, the imaging operation is terminated by the continuous imaging means on the basis of at least one condition selected from a distance of movement of the illumination optical system and the imaging optical system, the photoreception signal of reflected light from the cornea of the eye under examination, and elapsed time.

11. The cornea imaging apparatus according to claim 1, further comprising: memory means for saving photographic images taken by the photoelectric element; and image selecting means for sorting photographic images on the basis of photographic image light intensity level, contrast, or both, and saving the images in the memory means.

12. A cornea imaging apparatus comprising:
an illumination optical system having an illumination source for directing a slit light beam on a diagonal into an eye under examination;
an imaging optical system having a photoelectric element for receiving a reflected light beam produced by reflection of the slit light beam from a cornea of the eye under examination, and for imaging the cornea;
an actuating mechanism for moving the illumination optical system and the imaging optical system in totality in a direction nearer to or further from the eye under examination to bring about focusing;
an imaging process retracting control device adapted to control the actuating mechanism during an imaging operation by the imaging optical system, to retract the illumination optical system and the imaging optical system in a direction away from the eye under examination in a cross direction of the eye under examination;
a continuous imaging device adapted to take multiple images of the cornea at different times and positions by the photoelectric element of the imaging optical system during a retracting operation by the imaging process retracting control device; and
an imaging operation control device adapted to control imaging operation status of the cornea by the continuous imaging device during the retracting operation by the imaging process retracting control device, with reference to a photoreception signal of reflected light from the cornea of the eye under examination.

13. The cornea imaging apparatus according to claim 12, wherein the illumination sources of the illumination optical system comprises an imaging light source for imaging the cornea by means of guiding, into the photoelectric element of the imaging optical system, reflected light that has been directed into the eye under examination and reflected from the cornea; and with an output signal by the photoelectric element of reflected light produced by reflection by the cornea of an illuminating light beam from the imaging light source utilized as the photoreception signal, a cornea imaging operation status is controlled in the imaging operation control device on the basis of the output signal of the photoelectric element.

14. The cornea imaging apparatus according to claim 13, wherein with the output signal by the photoelectric element utilized as the photoreception signal, the cornea imaging operation status is controlled in the imaging operation control device on the basis of the output signal of the photoelectric element by means of controlled modification of a speed of the retracting operation by the imaging process retracting control device.

15. The cornea imaging apparatus according to claim 13, wherein with the output signal by the photoelectric element utilized as the photoreception signal, the cornea imaging operation status is controlled in the imaging operation control device on the basis of the output signal of the photoelectric element by means of controlled modification of a continuous imaging time interval of the cornea by the continuous imaging device.

16. The cornea imaging apparatus according to claim 12, wherein a position-sensing light source is employed as one of the illumination sources of the illumination optical system, separate from an imaging light source used for imaging the cornea by means of guiding, into the photoelectric element of the imaging optical system, reflected light that has been directed into the eye under examination and reflected from the cornea; a line sensor for receiving the reflected light produced by reflection by the cornea of an illuminating light beam is employed as the position-sensing light source; and with an output signal by the line sensor as utilized as the photoreception signal, the cornea imaging operation status is controlled in the imaging operation control device on the basis of the output signal of the line sensor.

17. The cornea imaging apparatus according to claim 16, wherein in the imaging operation control device, emission of light by the imaging light source and a cornea imaging operation by the continuous imaging device are controlled so as to be respectively initiated on a condition that reflected light from the cornea has been verified on the basis of the output signal of the line sensor.

18. The cornea imaging apparatus according to claim 17, wherein in the imaging operation control device, a detection level of an output signal is set to one corresponding to a prescribed intensity lower than that of an output signal corresponding to reflected light intensity at a focal location from a corneal endothelium detected by the line sensor.

19. The cornea imaging apparatus according to claim 12, further comprising: a pre-imaging process advancing control device adapted to control the actuating mechanism and advancing the illumination optical system and the imaging optical system in a direction closer to the eye under examination in the cross direction of the eye under examination, prior to the retracting operation by the imaging process retracting control device during the imaging operation; and a reversal operation control device adapted to control reversal of a direction of movement from advancing operation by the pre-imaging process advancing control device to the retracting operation by the imaging process retracting control device, on the basis of the photoreception signal of reflected light from the cornea of the eye under examination.

20. The cornea imaging apparatus according to claim 19, wherein a position-sensing light source is employed as one of the illumination sources of the illumination optical system, separate from an imaging light source used for imaging the cornea by means of guiding, into the photoelectric element of the imaging optical system, reflected light that has been directed into the eye under examination and reflected from the cornea; a line sensor for receiving the reflected light produced by reflection by the cornea of the illuminating light beam is employed as the position-sensing light source; an output signal of the line sensor is used as the photoreception signal of reflected light from the cornea of the eye under examination; and on the basis of the output signal of the line sensor, the direction of movement during the advancing operation by the pre-imaging process advancing control device is reversed by the reversal operation control device, at a reversal position established to a rear of an endothelium focal position.

21. The cornea imaging apparatus according to claim 12, wherein in the imaging operation control device, the imaging operation is terminated by the continuous imaging device on the basis of at least one condition selected from a distance of movement of the illumination optical system and the imaging optical system, the photoreception signal of reflected light from the cornea of the eye under examination, and elapsed time.

22. The cornea imaging apparatus according to claim 12, further comprising: a memory device adapted to save photographic images taken by the photoelectric element; and an image selecting device adapted to sort photographic images on the basis of photographic image light intensity level, contrast, or both, and save the images in the memory device.

\* \* \* \* \*